United States Patent
Say

(10) Patent No.: US 9,504,162 B2
(45) Date of Patent: Nov. 22, 2016

(54) MANUFACTURING ELECTROCHEMICAL SENSOR MODULES

(75) Inventor: James L. Say, Breckenridge, CO (US)

(73) Assignee: PEPEX BIOMEDICAL, INC., St. Louis, MO (US)

( * ) Notice: Subject to any disclaimer, the term of this patent is extended or adjusted under 35 U.S.C. 154(b) by 284 days.

(21) Appl. No.: 14/118,732

(22) PCT Filed: May 18, 2012

(86) PCT No.: PCT/US2012/038601
§ 371 (c)(1),
(2), (4) Date: Nov. 19, 2013

(87) PCT Pub. No.: WO2012/162151
PCT Pub. Date: Nov. 29, 2012

(65) Prior Publication Data
US 2015/0128412 A1    May 14, 2015

Related U.S. Application Data

(60) Provisional application No. 61/488,512, filed on May 20, 2011.

(51) Int. Cl.
*H05K 3/00* (2006.01)
*H01L 21/78* (2006.01)
*H01L 23/00* (2006.01)
*H01L 21/306* (2006.01)
(Continued)

(52) U.S. Cl.
CPC ............ *H05K 3/00* (2013.01); *G01N 27/3272* (2013.01); *H01L 21/306* (2013.01); *H01L 21/78* (2013.01); *H01L 24/82* (2013.01); *B81C 1/00317* (2013.01); *B81C 1/00333* (2013.01); *B81C 1/00888* (2013.01); *H01L 21/6836* (2013.01); *Y10T 29/49155* (2015.01)

(58) Field of Classification Search
CPC . H01L 24/82; H01L 21/306; H01L 21/6836; H01L 21/78; B81C 1/00317; B81C 1/00333; B81C 1/00888; H05K 3/00; G01N 27/3272; Y10T 29/49155
See application file for complete search history.

(56) References Cited

U.S. PATENT DOCUMENTS

| 1,454,224 A | 5/1923 | Schmidt |
| 2,291,720 A | 8/1942 | Hukle |

(Continued)

FOREIGN PATENT DOCUMENTS

| DE | 101 12 384 A1 | 9/2002 |
| DE | 10 2004 060 742 A1 | 7/2006 |

(Continued)

OTHER PUBLICATIONS

European Search Report for 09826755.2 mailed Oct. 5, 2012.
(Continued)

*Primary Examiner* — A. Dexter Tugbang
(74) *Attorney, Agent, or Firm* — Merchant & Gould P.C.

(57) ABSTRACT

Certain processes for manufacturing an electrochemical sensor module include etching a Silicon wafer to form precursor sensor bodies, disposing sensor fibers along rows of the precursor sensor bodies, securing a rigid layer over the sensor fibers, dividing the wafer, rigid layer, and sensor fibers into individual precursor sensor bodies, and joining each precursor sensor body to a component body to form sensor modules.

9 Claims, 7 Drawing Sheets

(51) Int. Cl.
  *G01N 27/327* (2006.01)
  *H01L 21/683* (2006.01)
  *B81C 1/00* (2006.01)

(56) References Cited

U.S. PATENT DOCUMENTS

| | | |
|---|---|---|
| 3,170,968 A | 2/1965 | Rokunohe et al. |
| 3,823,035 A | 7/1974 | Sanders |
| 3,926,201 A | 12/1975 | Katz |
| 4,008,302 A | 2/1977 | Erlichman |
| 4,008,717 A | 2/1977 | Kowarski |
| 4,073,974 A | 2/1978 | Albarino et al. |
| 4,224,125 A | 9/1980 | Nakamura et al. |
| 4,255,487 A | 3/1981 | Sanders |
| 4,296,533 A | 10/1981 | Doerter |
| 4,321,057 A | 3/1982 | Buckles |
| 4,399,099 A | 8/1983 | Buckles |
| 4,545,382 A | 10/1985 | Higgins et al. |
| 4,545,835 A | 10/1985 | Gusack et al. |
| 4,552,840 A | 11/1985 | Riffer |
| 4,573,968 A | 3/1986 | Parker |
| 4,640,821 A | 2/1987 | Mody et al. |
| 4,671,288 A | 6/1987 | Gough |
| 4,704,311 A | 11/1987 | Pickering et al. |
| 4,734,184 A | 3/1988 | Burleigh et al. |
| 4,820,399 A | 4/1989 | Senda et al. |
| 4,824,206 A | 4/1989 | Klainer et al. |
| 4,846,548 A | 7/1989 | Klainer |
| 4,880,752 A | 11/1989 | Keck et al. |
| 4,908,115 A | 3/1990 | Morita et al. |
| 4,919,649 A | 4/1990 | Timothy et al. |
| 4,927,516 A | 5/1990 | Yamaguchi et al. |
| 4,945,896 A | 8/1990 | Gade |
| 4,974,929 A | 12/1990 | Curry |
| 4,981,779 A | 1/1991 | Wagner |
| 5,001,054 A | 3/1991 | Wagner |
| 5,004,583 A | 4/1991 | Guruswamy et al. |
| RE33,677 E | 8/1991 | Vazirani |
| 5,047,044 A | 9/1991 | Smith et al. |
| 5,110,755 A * | 5/1992 | Chen .......... H01L 21/306 257/E21.215 |
| 5,112,455 A | 5/1992 | Cozzette et al. |
| 5,131,138 A | 7/1992 | Crouse |
| 5,164,229 A | 11/1992 | Hay et al. |
| 5,165,406 A | 11/1992 | Wong |
| 5,165,407 A | 11/1992 | Wilson et al. |
| 5,171,689 A | 12/1992 | Kawaguri et al. |
| 5,186,808 A | 2/1993 | Yamaguchi et al. |
| 5,205,920 A | 4/1993 | Oyama et al. |
| 5,217,533 A | 6/1993 | Hay et al. |
| 5,220,920 A | 6/1993 | Gharib |
| 5,243,982 A | 9/1993 | Möstl et al. |
| 5,244,636 A | 9/1993 | Walt et al. |
| 5,250,264 A | 10/1993 | Walt et al. |
| 5,262,035 A | 11/1993 | Gregg et al. |
| 5,264,092 A | 11/1993 | Skotheim et al. |
| 5,264,103 A | 11/1993 | Yoshioka et al. |
| 5,264,104 A | 11/1993 | Gregg et al. |
| 5,264,105 A | 11/1993 | Gregg et al. |
| 5,269,891 A | 12/1993 | Colin |
| 5,271,815 A | 12/1993 | Wong |
| 5,271,820 A | 12/1993 | Kinlen et al. |
| 5,277,872 A | 1/1994 | Bankert et al. |
| 5,298,144 A | 3/1994 | Spokane |
| 5,298,741 A | 3/1994 | Walt et al. |
| 5,320,725 A | 6/1994 | Gregg et al. |
| 5,320,814 A | 6/1994 | Walt et al. |
| 5,330,634 A | 7/1994 | Wong et al. |
| 5,356,786 A | 10/1994 | Heller et al. |
| 5,366,527 A | 11/1994 | Amos et al. |
| 5,372,133 A | 12/1994 | Hogen Esch |
| D354,347 S | 1/1995 | Knute et al. |
| D354,559 S | 1/1995 | Knute et al. |
| 5,384,028 A | 1/1995 | Ito |
| 5,395,504 A | 3/1995 | Saurer et al. |
| 5,422,246 A | 6/1995 | Koopal et al. |
| 5,431,174 A | 7/1995 | Knute |
| 5,437,973 A | 8/1995 | Vadgama et al. |
| 5,478,051 A | 12/1995 | Mauer |
| 5,503,728 A | 4/1996 | Kaneko et al. |
| 5,505,828 A | 4/1996 | Wong et al. |
| 5,512,159 A | 4/1996 | Yoshioka et al. |
| 5,543,012 A | 8/1996 | Watson et al. |
| 5,575,403 A | 11/1996 | Charlton et al. |
| 5,593,852 A | 1/1997 | Heller et al. |
| 5,605,152 A | 2/1997 | Slate et al. |
| 5,609,749 A | 3/1997 | Yamauchi et al. |
| 5,645,710 A | 7/1997 | Shieh |
| 5,656,241 A | 8/1997 | Seifert et al. |
| 5,720,924 A | 2/1998 | Eikmeier et al. |
| 5,810,199 A | 9/1998 | Charlton et al. |
| 5,824,177 A * | 10/1998 | Yoshihara .......... H01L 21/78 156/250 |
| 5,849,415 A | 12/1998 | Shalaby et al. |
| 5,863,800 A | 1/1999 | Eikmeier et al. |
| 5,900,215 A | 5/1999 | Seifert et al. |
| 5,951,764 A | 9/1999 | Hay et al. |
| 5,971,941 A | 10/1999 | Simons et al. |
| 5,972,199 A | 10/1999 | Heller et al. |
| 5,982,959 A | 11/1999 | Hopenfeld |
| 5,997,501 A | 12/1999 | Gross et al. |
| 6,036,924 A | 3/2000 | Simons et al. |
| 6,044,665 A | 4/2000 | Lysson et al. |
| 6,048,352 A | 4/2000 | Douglas et al. |
| D424,696 S | 5/2000 | Ray et al. |
| D426,638 S | 6/2000 | Ray et al. |
| 6,071,294 A | 6/2000 | Simons et al. |
| 6,071,391 A | 6/2000 | Gotoh et al. |
| 6,083,710 A | 7/2000 | Heller et al. |
| 6,103,033 A | 8/2000 | Say et al. |
| 6,103,199 A | 8/2000 | Bjornson et al. |
| 6,107,083 A | 8/2000 | Collins et al. |
| 6,120,676 A | 9/2000 | Heller et al. |
| 6,143,164 A | 11/2000 | Heller et al. |
| 6,241,863 B1 | 6/2001 | Montbouquette |
| 6,299,757 B1 | 10/2001 | Feldman et al. |
| 6,329,161 B1 | 12/2001 | Heller et al. |
| 6,338,790 B1 | 1/2002 | Feldman et al. |
| 6,379,317 B1 | 4/2002 | Kintzig et al. |
| 6,461,496 B1 | 10/2002 | Feldman et al. |
| 6,464,849 B1 | 10/2002 | Say et al. |
| 6,503,381 B1 | 1/2003 | Gotoh et al. |
| 6,560,471 B1 | 5/2003 | Heller et al. |
| 6,561,989 B2 | 5/2003 | Whitson |
| 6,576,101 B1 | 6/2003 | Heller et al. |
| 6,591,125 B1 | 7/2003 | Buse et al. |
| 6,592,745 B1 | 7/2003 | Feldman et al. |
| 6,607,658 B1 | 8/2003 | Heller et al. |
| 6,610,978 B2 | 8/2003 | Yin et al. |
| 6,616,819 B1 | 9/2003 | Liamos et al. |
| 6,618,934 B1 | 9/2003 | Feldman et al. |
| 6,620,112 B2 | 9/2003 | Klitmose |
| 6,676,816 B2 | 1/2004 | Mao et al. |
| 6,706,159 B2 | 3/2004 | Moerman et al. |
| 6,707,554 B1 | 3/2004 | Miltner et al. |
| 6,740,214 B1 | 5/2004 | Dobson et al. |
| 6,749,740 B2 | 6/2004 | Liamos et al. |
| 6,783,502 B2 | 8/2004 | Orloff et al. |
| 6,797,214 B1 | 9/2004 | Ruuttu et al. |
| 6,840,912 B2 | 1/2005 | Kloepfer et al. |
| 6,881,551 B2 | 4/2005 | Heller et al. |
| 6,893,545 B2 | 5/2005 | Gotoh et al. |
| 6,965,791 B1 | 11/2005 | Hitchcock et al. |
| 7,008,799 B1 | 3/2006 | Zimmer et al. |
| 7,058,437 B2 | 6/2006 | Buse et al. |
| 7,211,437 B2 | 5/2007 | Schabbach et al. |
| 7,264,139 B2 | 9/2007 | Brickwood et al. |
| 7,282,705 B2 | 10/2007 | Brennen |
| 7,299,081 B2 | 11/2007 | Mace et al. |
| 7,322,942 B2 | 1/2008 | Roe |
| 7,335,294 B2 | 2/2008 | Heller et al. |
| 7,344,499 B1 | 3/2008 | Prausnitz et al. |
| 7,378,007 B2 | 5/2008 | Moerman et al. |
| 7,396,334 B2 | 7/2008 | Kuhr et al. |

(56) References Cited

U.S. PATENT DOCUMENTS

| | | |
|---|---|---|
| 7,585,278 B2 | 9/2009 | Aceti et al. |
| 7,723,099 B2 | 5/2010 | Miller et al. |
| 7,740,581 B2 | 6/2010 | Buse et al. |
| 7,828,749 B2 | 11/2010 | Douglas et al. |
| 7,829,023 B2 | 11/2010 | Burke et al. |
| 7,860,544 B2 | 12/2010 | Say et al. |
| 7,875,228 B2 | 1/2011 | Storrs et al. |
| 2002/0040208 A1 | 4/2002 | Flaherty et al. |
| 2002/0098124 A1 | 7/2002 | Bentsen et al. |
| 2003/0211619 A1 | 11/2003 | Olson et al. |
| 2004/0087033 A1 | 5/2004 | Schembri |
| 2004/0102717 A1 | 5/2004 | Qi |
| 2004/0236251 A1 | 11/2004 | Roe et al. |
| 2005/0067737 A1 | 3/2005 | Mills et al. |
| 2005/0089944 A1 | 4/2005 | Shieh et al. |
| 2005/0196747 A1 | 9/2005 | Stiene |
| 2005/0197548 A1 | 9/2005 | Dietiker |
| 2006/0241517 A1 | 10/2006 | Fowler et al. |
| 2007/0027385 A1 | 2/2007 | Brister et al. |
| 2007/0123803 A1 | 5/2007 | Fujiwara et al. |
| 2007/0149897 A1 | 6/2007 | Ghesquiere et al. |
| 2007/0199818 A1 | 8/2007 | Petyt et al. |
| 2007/0218281 A1 | 9/2007 | Demir et al. |
| 2008/0017645 A1 | 1/2008 | Garagiola |
| 2008/0097546 A1 | 4/2008 | Powers et al. |
| 2008/0167578 A1 | 7/2008 | Bryer et al. |
| 2008/0295328 A1* | 12/2008 | Sasaki ............... H01L 24/82 29/831 |
| 2009/0021901 A1 | 1/2009 | Stothers |
| 2009/0032760 A1 | 2/2009 | Muscatell |
| 2009/0056447 A1* | 3/2009 | Berthold ............ H01L 21/306 73/514.26 |
| 2009/0069654 A1 | 3/2009 | Yasuzawa et al. |
| 2009/0178923 A1 | 7/2009 | Marquant et al. |
| 2009/0257917 A1 | 10/2009 | Nakamura et al. |
| 2010/0018869 A1 | 1/2010 | Feldman et al. |
| 2010/0018871 A1 | 1/2010 | Feldman et al. |
| 2010/0051479 A1 | 3/2010 | Heller et al. |
| 2010/0059372 A1 | 3/2010 | Heller et al. |
| 2010/0059373 A1 | 3/2010 | Heller et al. |
| 2010/0072063 A1 | 3/2010 | Heller et al. |
| 2010/0072064 A1 | 3/2010 | Heller et al. |
| 2010/0267183 A1* | 10/2010 | Kramer ............ B81C 1/00333 438/51 |
| 2010/0326842 A1 | 12/2010 | Mazza et al. |
| 2011/0000610 A1 | 1/2011 | Burke et al. |
| 2011/0028815 A1 | 2/2011 | Simpson et al. |
| 2011/0086373 A1 | 4/2011 | Wallace-Davis et al. |
| 2011/0189762 A1 | 8/2011 | Say |
| 2011/0203941 A1 | 8/2011 | Say |
| 2011/0265944 A1 | 11/2011 | Say |
| 2011/0266149 A1 | 11/2011 | Say |
| 2011/0270061 A1 | 11/2011 | Say |
| 2012/0291254 A1 | 11/2012 | Say |

FOREIGN PATENT DOCUMENTS

| | | |
|---|---|---|
| EP | 0 256 415 A2 | 2/1988 |
| EP | 0 327 658 A1 | 8/1989 |
| EP | 0 409 033 A2 | 1/1991 |
| EP | 0 420 296 A1 | 4/1991 |
| EP | 0 592 805 A2 | 4/1994 |
| EP | 0 710 835 A2 | 5/1996 |
| EP | 0 792 620 A2 | 9/1997 |
| EP | 0 965 301 A1 | 12/1999 |
| EP | 1 462 775 | 9/2004 |
| JP | 64-3552 | 1/1989 |
| JP | 1-153952 | 6/1989 |
| JP | 1-263537 | 10/1989 |
| JP | 4-279854 | 10/1992 |
| JP | 6-174946 | 6/1994 |
| JP | 8-107890 | 4/1996 |
| JP | 08327486 A * | 12/1996 |
| JP | 2007-202632 | 8/2007 |
| WO | WO 89/07139 | 8/1989 |
| WO | WO 91/15993 | 10/1991 |
| WO | WO 94/10553 | 5/1994 |
| WO | WO 96/22730 | 8/1996 |
| WO | WO 96/39616 | 12/1996 |
| WO | WO 97/15827 | 5/1997 |
| WO | WO 00/35340 | 6/2000 |
| WO | WO 2005/051183 A1 | 6/2005 |
| WO | WO 2007/091633 A1 | 8/2007 |
| WO | WO 2008/017645 A1 | 2/2008 |
| WO | WO 2009/032760 | 3/2009 |
| WO | WO 2009/051901 | 4/2009 |
| WO | WO 2010/056869 | 5/2010 |
| WO | WO 2010/056878 | 5/2010 |
| WO | WO 2010/056878 A2 | 5/2010 |

OTHER PUBLICATIONS

Gough, D. et al., "Short-term In Vivo operation of a glucose sensor," *A.S.A.I.O. Transactions*, vol. 32, No. 1, pp. 148-150 (Jul.-Sep. 1986).

International Search Report and Written Opinion for PCT/US2008/074649 mailed Apr. 20, 2009.

International Search Report and Written Opinion for PCT/US2008/074644 mailed May 14, 2009.

International Search Report and Written Opinion for PCT/US2009/064216 mailed May 3, 2010.

International Search Report and Written Opinion for PCT/US2009/064225 mailed May 4, 2010.

International Search Report and Written Opinion for PCT/US2009/064228 mailed Jul. 1, 2010.

Jaraba, P. et al., "NADH amperometric sensor based on poly(3-methylthiophene)-coated cylindrical carbon fiber microelectrodes: application to the enzymatic determination of L-lactate," *Electrochimika Acta.*, vol. 43, No. 23, pp. 3555-3565 (1998).

Netchiporouk, L.I. et al., "Properties of carbon fibre microelectrodes as a basis for enzyme biosensors," *Analytica Chimica Acta*, vol. 303, pp. 275-283 (1995).

Sakslund, H. et al., "Development and evaluation of glucose microsensors based on electrochemical codeposition of ruthenium and glucose oxidase onto carbon fiber microelectrodes," *Journal of Electroanalytical Chemistry*, vol. 397, pp. 149-155 (1995).

Sakslund, H. et al, "Analysis of the factors determining the sensitivity of a miniaturized glucose biosensor made by codeposition of palladium and glucose oxidase onto an 8 μm carbon filter," *Journal of Electroanalytical Chemistry*, vol. 402, pp. 149-160 (1996).

International Search Report and Written Opinion from International Application No. PCT/US2012/038601 filed May 18, 2012.

U.S. Appl. No. 61/430,384, filed Jan. 6, 2011.

\* cited by examiner

MANUFACTURING ELECTROCHEMICAL SENSOR MODULES

This application is a National Stage Application of PCT/US2012/038601, filed 18 May 2012, which claims benefit of U.S. Provisional Application Ser. No. 61/488,512 filed May 20, 2011, the subject matter of which is incorporated by reference in its entirety. To the extent appropriate, a claim of priority is made to each of the above disclosed applications.

TECHNICAL FIELD

The present disclosure relates to manufacturing systems and processes for producing sensors for measuring bioanalytes and, in particular, to producing sensors using continuous manufacturing systems and processes.

BACKGROUND

Electrochemical bio-sensors have been developed for detecting analyte concentrations in a given fluid sample. For example, U.S. Pat. Nos. 5,264,105; 5,356,786; 5,262,035; 5,320,725; and 6,464,849, which are hereby incorporated herein by reference in their entireties, disclose wired enzyme sensors for detecting analytes, such as lactate or glucose. Wired enzyme sensors have been widely used in blood glucose monitoring systems adapted for home use by diabetics to allow blood glucose levels to be closely monitored. Other example types of blood glucose monitoring systems are disclosed by U.S. Pat. Nos. 5,575,403; 6,379,317; and 6,893,545.

Conventional manufacturing systems and processes for producing bio-sensors involve web based conductive print technology.

SUMMARY

One aspect of the present disclosure relates to a sensor system that can be manufactured in reduced scale and that can be conveniently handled by consumers.

Another aspect of the present disclosure relates to an electrochemical sensor module for use in a sensor system that can be efficiently manufactured using a continuous manufacturing process such as a continuous insert molding process.

A further aspect of the present disclosure relates to a sensor module including a molded body that defines an analyte analysis cell and also integrates a skin piercing element, such as a lancet or canula, into the molded body.

A variety of additional aspects will be set forth in the description that follows. The aspects can relate to individual features and to combinations of features. It is to be understood that both the forgoing general description and the following detailed description are exemplary and explanatory only and are not restrictive of the broad concepts upon which the embodiments disclosed herein are based.

DETAILED DESCRIPTION

Figure 1:
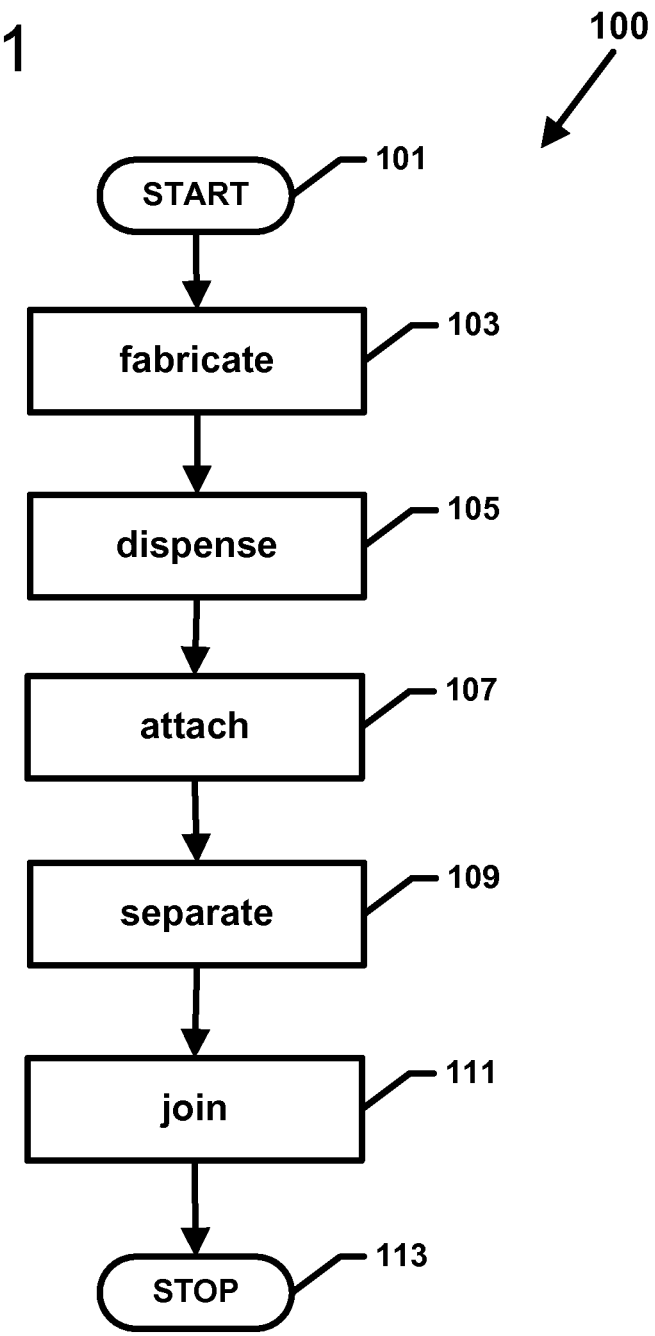
FIG. 1 is a flowchart illustrating an operational flow for a manufacturing process by which multiple sensor modules may be produced.

Reference will now be made in detail to exemplary aspects of the present disclosure which are illustrated in the accompanying drawings. Wherever possible, the same reference numbers will be used throughout the drawings to refer to the same or like parts.

The following definitions are provided for terms used herein:

A "working electrode" is an electrode at which the analyte (or a second compound whose level depends on the level of the analyte) is electrooxidized or electroreduced with or without the agency of an electron transfer agent.

A "reference electrode" is an electrode used in measuring the potential of the working electrode. The reference electrode should have a generally constant electrochemical potential as long as no current flows through it. As used herein, the term "reference electrode" includes pseudo-reference electrodes. In the context of the disclosure, the term "reference electrode" can include reference electrodes which also function as counter electrodes (i.e., a counter/reference electrode).

A "counter electrode" refers to an electrode paired with a working electrode to form an electrochemical cell. In use, electrical current passes through the working and counter electrodes. The electrical current passing through the counter electrode is equal in magnitude and opposite in sign to the current passing through the working electrode. In the context of the disclosure, the term "counter electrode" can include counter electrodes which also function as reference electrodes (i.e., a counter/reference electrode).

A "counter/reference electrode" is an electrode that functions as both a counter electrode and a reference electrode.

An "electrochemical sensing system" is a system configured to detect the presence and/or measure the level of an analyte in a sample via electrochemical oxidation and reduction reactions on the sensor. These reactions are converted (e.g., transduced) to an electrical signal that can be correlated to an amount, concentration, or level of an analyte in the sample. Further details about electrochemical sensing systems, working electrodes, counter electrodes and reference electrodes can be found at U.S. Pat. No. 6,560,471, the disclosure of which is hereby incorporated herein by reference in its entirety.

"Electrolysis" is the electrooxidation or electroreduction of a compound either directly at an electrode or via one or more electron transfer agents.

An "electron transfer agent" is a compound that carries electrons between the analyte and the working electrode either directly or in cooperation with other electron transfer agents. One example of an electron transfer agent is a redox mediator.

A "sensing layer" is a component of the sensor which includes constituents that facilitate the electrolysis of the analyte. The sensing layer may include constituents such as an electron transfer agent, a catalyst which catalyzes a reaction of the analyte to produce a response at the electrode, or both.

The present disclosure is directed to a manufacturing system configured to produce one or more sensor modules configured for analyte monitoring (e.g., glucose single-point monitoring, lactate single-point monitoring, etc.). Each sensor module includes a housing containing an analysis cell configured to hold a fluid sample, at least two elongated electrodes arranged to enter the analysis cell, and contacts for electrically connecting the electrodes to external connectors. Certain types of the elongated electrodes includes a composite conductive monofilament (CCM) electrode. In other embodiments, the housing can contain additional electrodes having differing enzyme coatings. The analysis cell can be configured for coulormetric or amperometric assays.

FIG. 1 is a flowchart illustrating an operational flow for a manufacturing process 100 by which multiple sensor modules may be produced. In some implementations, the manufacturing process 100 uses microfabrication technology to produce multiple precursor bodies of sensor modules on a single wafer. For example, in certain implementations, the manufacturing process 100 produces about 900 sensors on a six-inch diameter substrate. In other implementations, the manufacturing process 100 can produce greater or fewer sensors on larger or smaller substrate.

The manufacturing process 100 begins at a start module 101, performs any appropriate initialization procedures, and proceeds to a fabricate operation 103. The fabricate operation 103 forms features of one or more precursor sensor bodies in a wafer of substrate 120. In accordance with some aspects, the fabricate operation 103 removes material from the wafer, for example, to form wells and/or channels in the substrate. In some implementations, the fabricate operation 103 removes the material through etching. In other implementations, the fabricate operation 103 removes the material using a laser. In accordance with other aspects, the fabricate operation 103 deposits material into the wafer, for example, to form conductive signal paths or other features.

A dispense operation 105 disposes one or more electrodes along the features of the precursor sensor bodies. In some implementations, the dispense operation 105 disposes a single sensor fiber along the features of multiple precursor sensor bodies. In certain implementations, the dispense operation 105 disposes two sensor fibers (e.g., a working electrode and a counter electrode) along the features of multiple precursor sensor bodies. In certain implementations, the dispense operation 105 disposes three sensor fibers (e.g., a working electrode, a counter electrode, and a reference electrode) along the features of multiple precursor sensor bodies.

An attach operation 107 secures a rigid layer to the wafer 120. In certain implementations, the attach operation 107 secures the rigid layer to the wafer 120 using an organic binder. The rigid layer cooperates with the fabricated substrate 120 to define features (e.g. a test chamber) of the precursor sensor bodies. The rigid layer also secures the electrodes in the precursor sensor bodies. In certain implementations, the binder also provides a seal around the electrodes.

A separate operation 109 divides the wafer into segments so that each segment contains the features of a single precursor sensor body. In certain implementations, dicing tape is applied to the wafer to protect the sensor features during the separate operation 109. In some implementations, the separate operation 107 divides the wafer by cutting the wafer using a shear or other blade. In other implementations, the separate operation 109 divides the wafer using a laser. In still other implementations, the separate operation 109 divides the wafer by scoring and bending the wafer.

A join operation 111 couples the wafer segment to one or more additional components. When joined, the features of the wafer segment and features of the additional components form a complete sensor body. For example, in certain implementations, joining the wafer and the additional components seals an analysis cell of the sensor body. In certain implementations, joining the wafer and the additional components provides capillary channels from the analysis cell to an exterior of the sensor body. In some implementations, the join operation 111 couples the wafer segment to a molded carrier. In other implementations, the join operation 111 couples the wafer segment to a laminated section.

The manufacturing process 100 performs any appropriate completion procedures and ends at a stop module 113.

FIGS. 2-12 illustrate the steps of the manufacturing process 100 as applied to one example implementation. In the example shown, the manufacturing process 100 is used to form six sensor modules 150. Each sensor module 150 includes a precursor sensor body 140 and a component body 151. The precursor sensor body 140 includes a first (e.g., working) electrode 130 and a second (e.g., counter) electrode 131 disposed in holding structures 122, 123 that extend between opposite ends of the sensor body 150. The electrodes 130, 131 also extend through a test chamber 155 configured to hold a blood sample from a patient. Each precursor sensor body 140 also includes electrode contacts 124, 126 that carry signals from the electrodes 130, 131 to a monitoring system coupled to the sensor module 150. The component body 151 defines a capillary port through which a blood sample may enter the test chamber 155. Certain types of component bodies 151 also include skin-piercing members.

Figure 2:
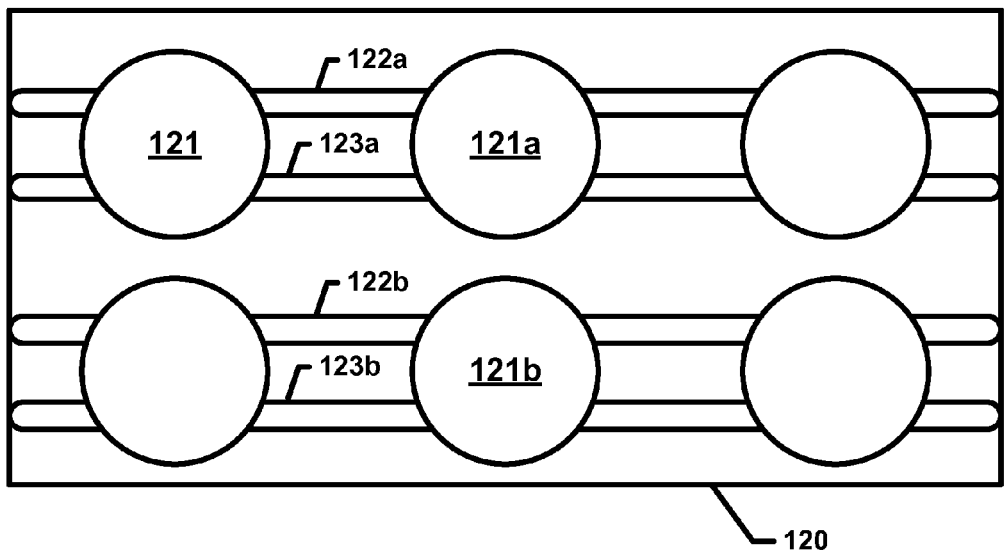
FIG. 2 is a top, plan view of an example wafer with features of precursor sensor bodies etched into a surface.
Figure 3:
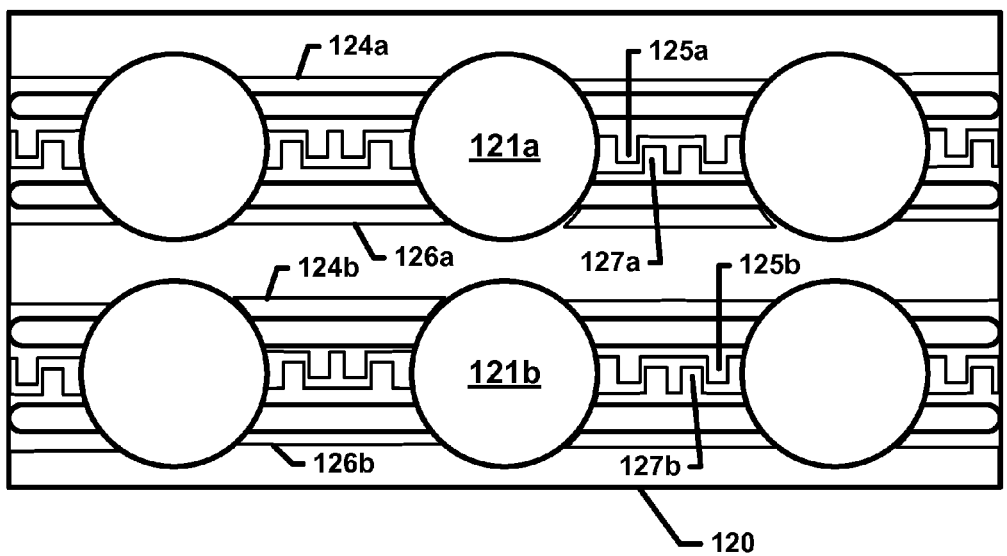
FIG. 3 is a top, plan view of the wafer of FIG. 2 with conductive tracings deposited over the etched features.

FIGS. 2 and 3 show the results of the fabricate operation 103 implemented on an example wafer 120. In the example shown, the wafer 120 has a rectangular shape. In other implementations, however, the wafer 120 may be round, oblong, square, triangular, or any other shape. In some implementations, the wafer 120 is a Silicon wafer. In other implementations, however, the wafer 120 may be formed from any suitable substrate material.

As shown in FIG. 2, the fabricate operation 103 removes material from the wafer 120 to form features of multiple precursor sensor bodies 140. The fabricate operation 103 forms at least a first row of precursor sensor bodies 140 on the substrate 120. Each row includes features from at least one precursor sensor body 140. In certain implementations, each row includes features from multiple precursor sensor bodies 140. In some implementations, the fabricate operation 103 forms multiple rows of precursor sensor body features. In other implementations, the fabricate operation 103 may form precursor sensor body features in the wafer 120 in other configurations or patterns (e.g., rings, matrices, staggered rows, etc.).

In some implementations, the fabricate operation 103 removes material to define one or more wells 121. Each well 121 corresponds to one precursor sensor body 140. The well 121 of each precursor sensor body 140 is configured to form part of the test chamber of a respective assembled sensor body 150. In some implementations, the fabricate operation 103 also removes material to form at least a first channel 122 for each precursor sensor body. In certain implementations, the fabricate operation 103 forms a continuous channel extending across the wafer 120 to form the first channel 122 for each precursor sensor body 140 in the row. In certain implementations, the fabricate operation 103 also forms a second channel 123 extending through one or more of the precursor sensor bodies 140 in each row.

In the example shown in FIG. 2, the fabricate operation 103 forms two rows of features of precursor sensor bodies 140. Each row includes features of three precursor sensor bodies 140. For example, the fabricate operation 103 forms a well 121a for each precursor sensor body 140 in the first row and a well 121b for each precursor sensor body 140 in the second row. The fabricate operation 103 also forms a first groove 122a and a second holding groove 123a that extends across the wafer 120 through the first row of precursor sensor bodies 140. The fabricate operation 103 also forms a first groove 122b and a second groove 123b that extends across the wafer 120 through the second row of precursor sensor bodies 140.

In some implementations, the fabricate operation 103 deposits material on the wafer 120 to form features of the precursor sensor bodies 140. For example, the fabricate operation 103 may deposit a metal or other conductive material over the wafer 120 to form one or more conductive paths across the wafer 120. As shown in FIG. 3, in some implementations, the fabricate operation 103 forms a first conductive path 124 along the first groove 122 and a second conductive path 126 along the second groove 123. In certain implementations, the conductive paths 124, 126 are broken by the wells 121. In other implementations, the conductive paths 124, 126 pass through the wells 121.

In some implementations, the first conductive path 124 includes at least one contact pad 125 for each precursor sensor body 140 and the second conductive path 126 includes at least one contact pad 127 for each precursor sensor body 140. In certain implementations, each of the conductive paths 124, 126 includes two contact pads 125, 127 for each precursor sensor body 140. For example, each conductive path 124, 126 may include a corresponding contact pad 125, 127, respectively, on either side of the well 121.

Figure 4:
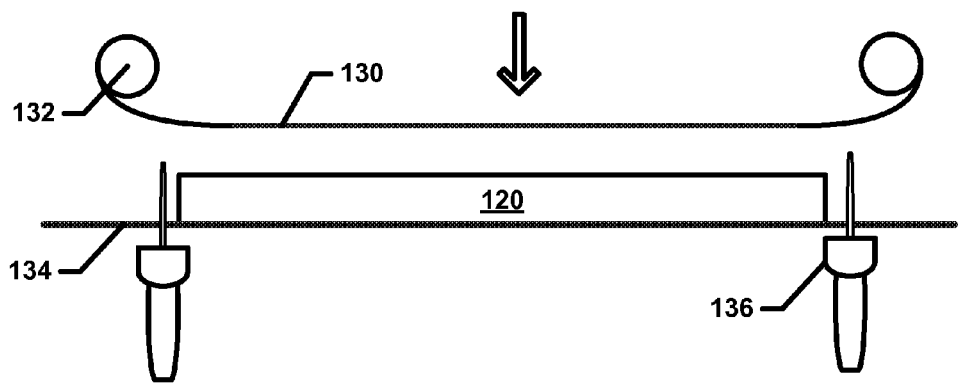
FIG. 4 illustrates one example implementation of a manufacturing station at which the dispense operation of FIG. 1 is implemented.

FIG. 4 illustrates one example implementation of a manufacturing station 134 at which the dispense operation 105 is implemented. The first station 134 is configured to deposit one or more sensor fiber electrodes onto the substrate wafer 120. In one example implementation, each sensor fiber electrode includes a composite sensor fiber having a dielectric core, a conductive layer, and a sensing layer. In some implementations, the manufacturing station 134 deposits a single sensor fiber 130 onto the wafer 120 for each row of precursor sensor bodies 140. In other implementations, the manufacturing station 134 disposes multiple sensor fiber electrodes onto the wafer 120 per row of precursor sensor bodies 140. For example, the first station 134 may dispose a first sensor fiber (e.g., working electrode) 130 and a second sensor fiber (e.g., counter electrode) 131 onto each row of the wafer 120.

Figure 5:
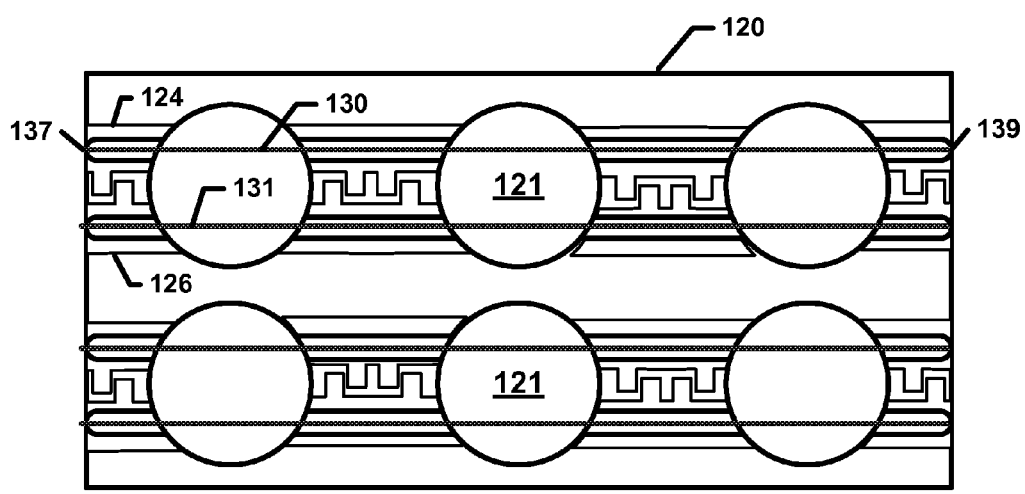
FIG. 5 is a top, plan view of the wafer of FIG. 3 with sensor fibers disposed across the etched features.

In some implementations, the composite sensor fibers are dispensed from one or more reels 132 into the grooves 122, 123 defined in the precursor sensor bodies 140. In certain implementations, the first station 134 includes a set of reels 132 for each row of precursor sensor bodies 140. In other implementations, the first station 134 includes multiple sets of reels 132 for each row of precursor sensor bodies 140, each set dispensing one sensor fiber onto a groove. For example, as shown in FIG. 5, a first sensor fiber 130 may be disposed along a first groove 124 and a second sensor fiber 131 may be disposed along a second groove 126 for each row of precursor sensor bodies 140.

In certain implementations, the first station 901 also includes one or more cutting structures 136 that disconnect the dispensed sensor fibers 906 from the reels 910. In some implementations, the cutting structures 914 cut the sensor fibers 130, 131 at extreme ends of the wafer 120. In such implementations, a continuous length of each sensor fiber 130, 131 extends through all of the precursor sensor bodies 140 in one of the rows of precursor sensor bodies 140. In the example shown in FIG. 5, a first continuous length of sensor fiber 130 extends from a first cut end 137 to a second cut end 139. The first cut end 137 is located at a first end of the wafer 120 and the second cut end 139 is located at an opposite end of the wafer 120. Each of the other sensor fibers in FIG. 5 also extend through multiple precursor sensor bodies 140 between opposite sides of the wafer 120.

In some implementations, the dispose operation 105 also includes disposing a binder over the fiber sensors 130, 131. In certain implementations, the binder is an organic binder that is configured to permanently attach a rigid layer to the silicone substrate 120. In certain implementations, the binder also provides a thin film that forms a seal around the sensor fibers 130, 131.

Figure 6:
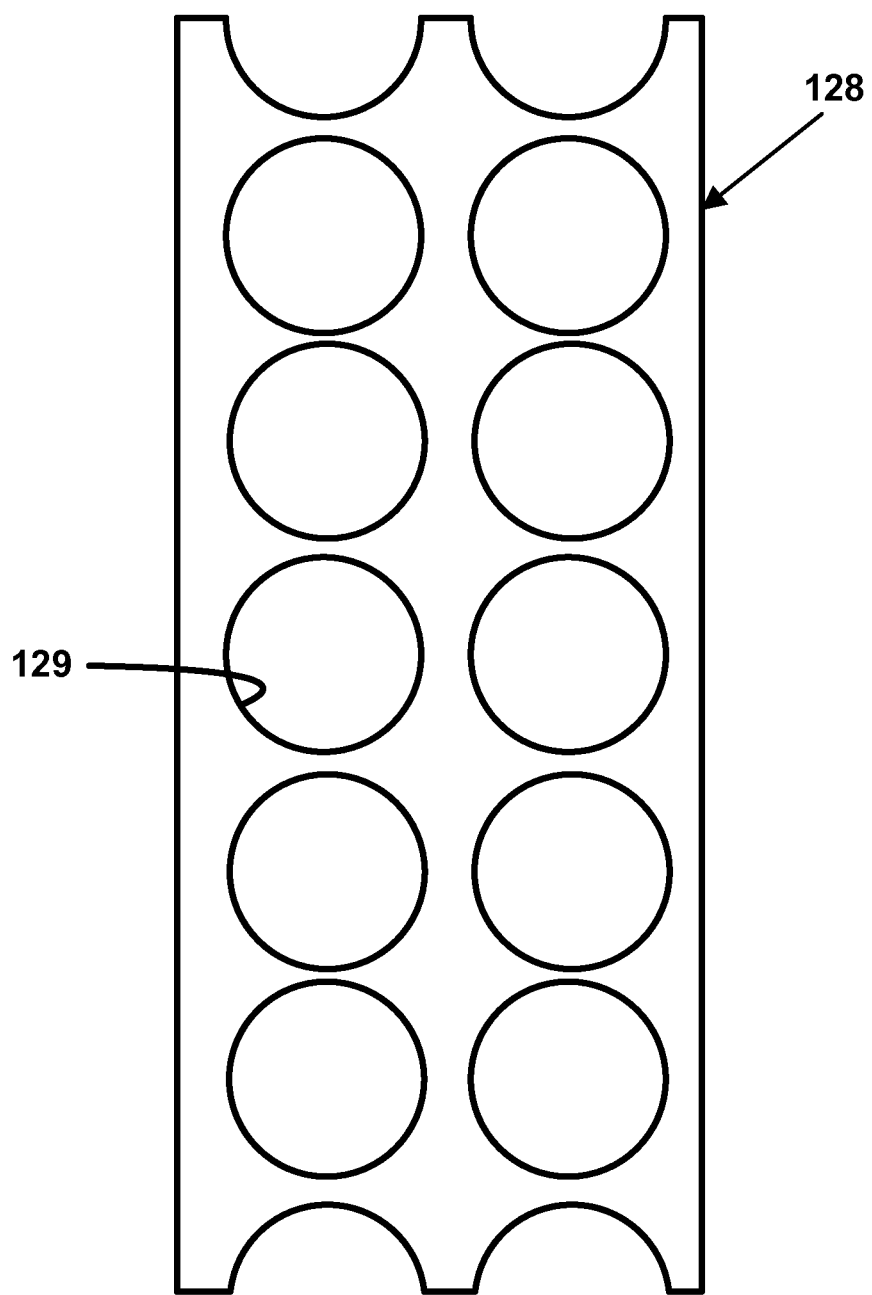
FIG. 6 is a top, plan view of an example rigid layer suitable for use with the wafer of FIG. 5.
Figure 7:
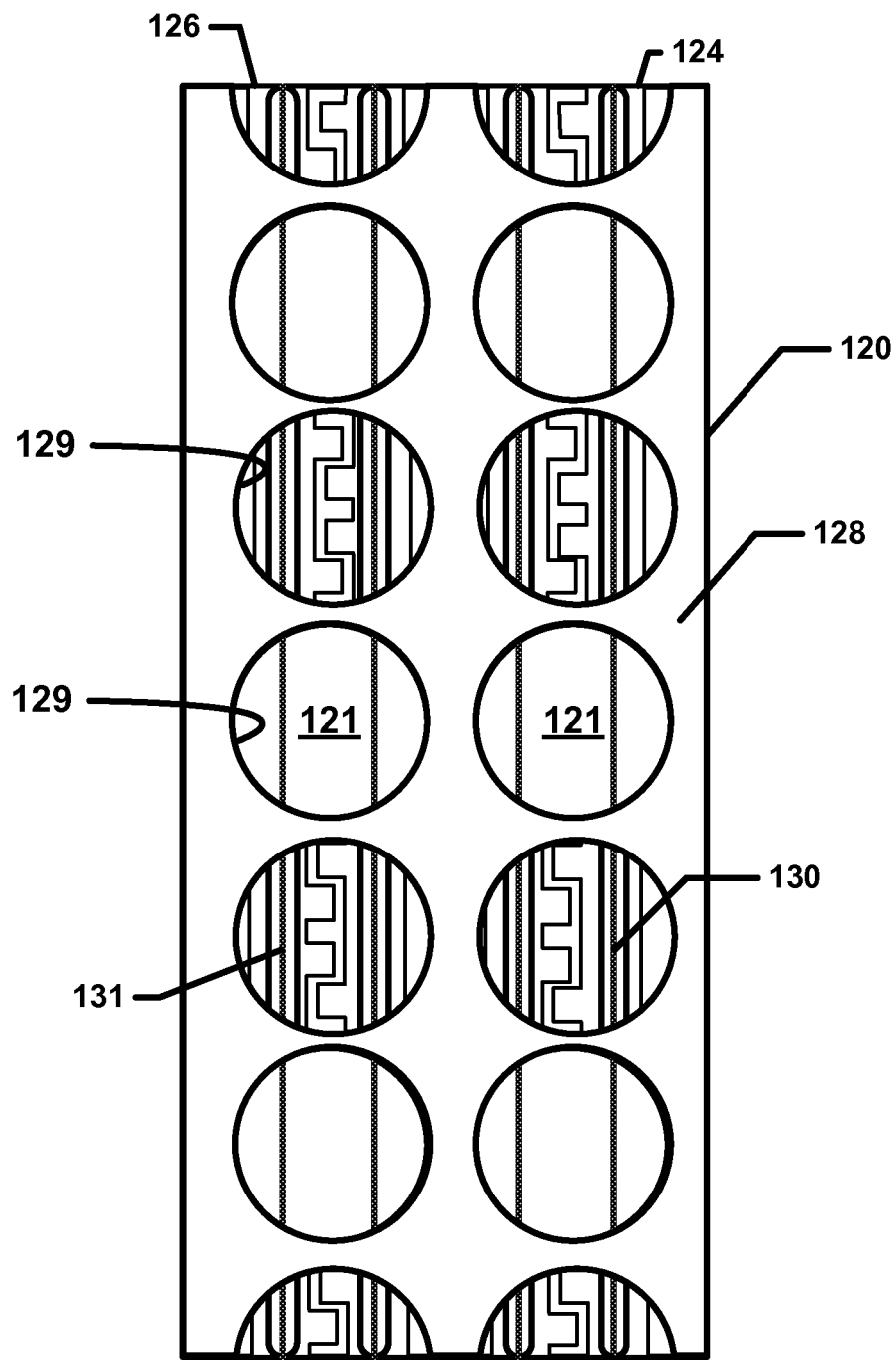
FIG. 7 shows the rigid layer of FIG. 6 attached to the wafer of FIG. 5.

FIGS. 6 and 7 illustrate an example implementation of a rigid layer 128 suitable to be secured to the wafer 120 to form the precursor sensor bodies 140. The rigid layer 128 defines a plurality of apertures 129. In some implementations, the rigid layer 128 defines apertures 129 that align with the wells 121 of the wafer 120 to form the test chambers 155 of the precursor sensor bodies 140 (see FIG. 7). In certain implementations, the rigid layer 128 also defines apertures 129 that align between the wells 121 of the wafer 120 to expose the contact pads 125, 127 of the precursor sensor bodies 140 (see FIG. 7). Accordingly, a monitoring system can access signals generated by the electrodes via the contact pads 125, 127.

Figure 8:
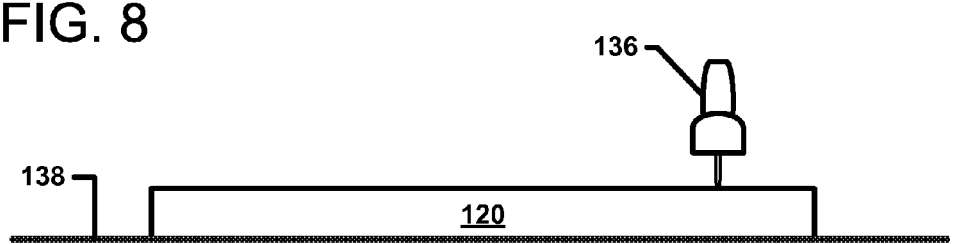
FIG. 8 illustrates one example implementation of a cutting station at which the separate operation of FIG. 1 is implemented.
Figure 9:
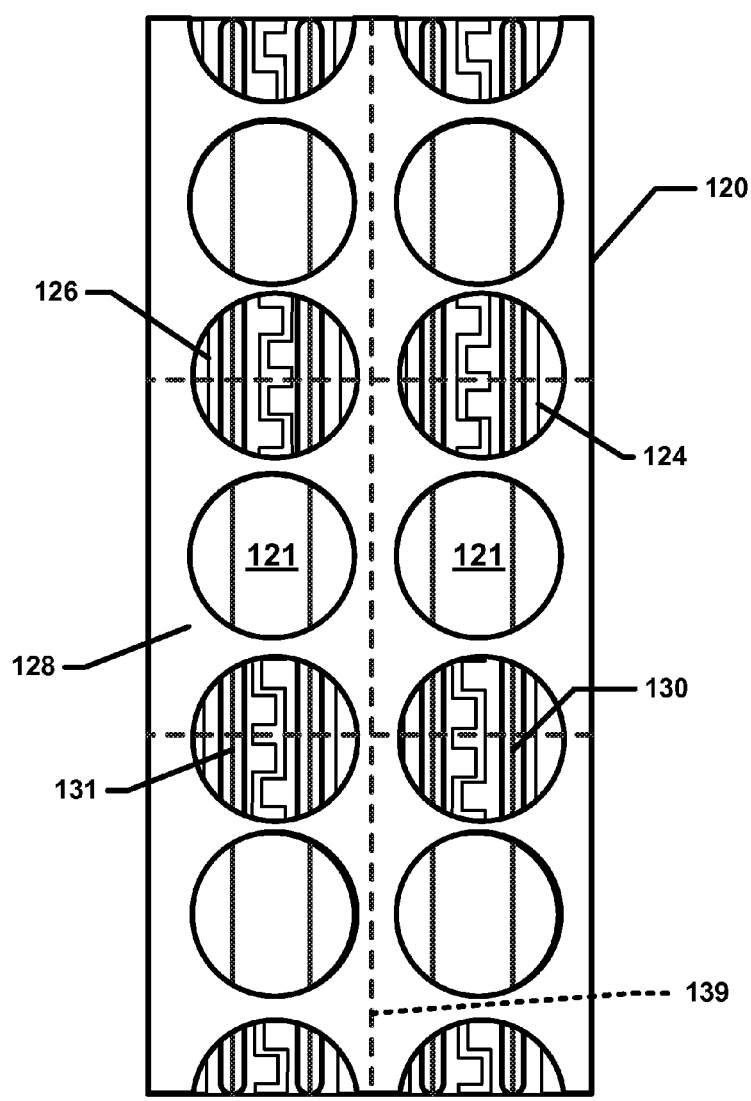
FIG. 9 shows cutting paths superimposed over the rigid layer.

FIG. 8 illustrates one example implementation of a cutting station 138 of the manufacturing system. The cutting station 138 is configured to separate the precursor bodies 140 of the sensor modules 150 from each other by cutting the wafer 120 and the continuous lengths of the composite sensor fibers 130, 131. For example, FIG. 9 shows cutting paths 139 superimposed over the rigid layer 128. The cutting paths 139 define the boundaries of the precursor sensor bodies 140.

The cutting station 138 includes at least one cutting tool 136. In some implementations, the cutting station 138 includes a single cutting tool 136 that moves along the wafer 120. In other implementations, the cutting station 138 includes multiple cutting tools 136. For example, the cutting tools 136 may be positioned in a fixed pattern and pressed through the wafer 120. In certain implementations, the cutting station 138 applies dicing tape to a top of the wafer 120 along dividing lines that define the boundaries of the precursor sensor bodies 140. The dicing tape may protect the sensor fibers 130, 131 or other features while the wafer is segmented.

In some implementations, the wafer 120 and sensor fibers 130, 131 are cut using the same cutting tool 136. In certain implementations, the wafer 120 and the sensor fibers 130, 131 are cut with a laser. In certain implementations, the wafer 120 and sensor fibers 130, 131 are cut with a knife or other bladed instrument. In certain implementations, the wafer 120 and sensor fibers 130, 131 are cut with a nipper. In certain implementations, the wafer 120 and sensor fibers 130, 131 are cut with pneumatic shears. In other implementations, the wafer 120 and sensor fibers 130, 131 are cut using different tools. For example, the wafer 120 may be cut with a laser and the sensor fibers 130, 131 may be cut using a nipper.

Figure 10:
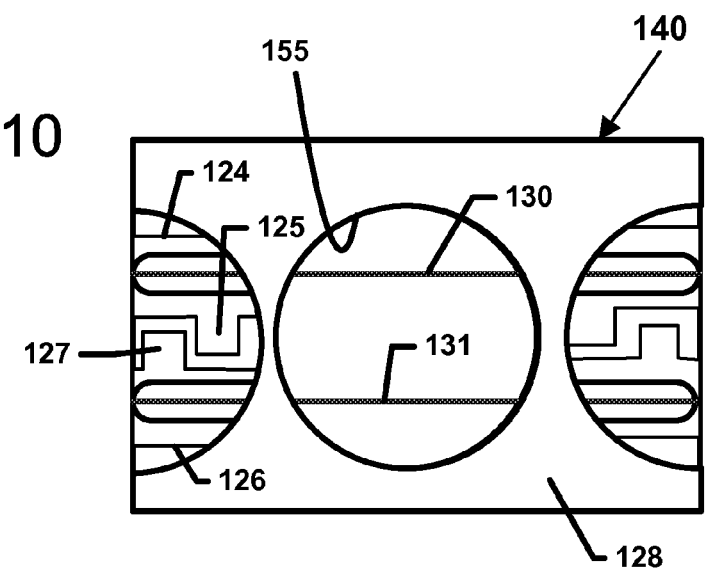
FIG. 10 shows one example precursor sensor body divided out from the wafer 120.

FIG. 10 shows one example segment divided out from the wafer 120. The segment defines a precursor sensor body 140 a first sensor fiber 130 and a second sensor fiber 131 extending through a test chamber 155. Cut ends of the sensor fibers 130, 131 are located at opposite sides of the test precursor sensor body 140. The aperture 129 in the rigid layer 128 provides access to the test chamber 155. Apertures 129 in the rigid layer 128 on either side of the test chamber 155 provide access to the contact pads 125, 127. The contact pads 125, 127 are located at positions offset from the cut ends of the electrodes 130, 131.

Figure 11:
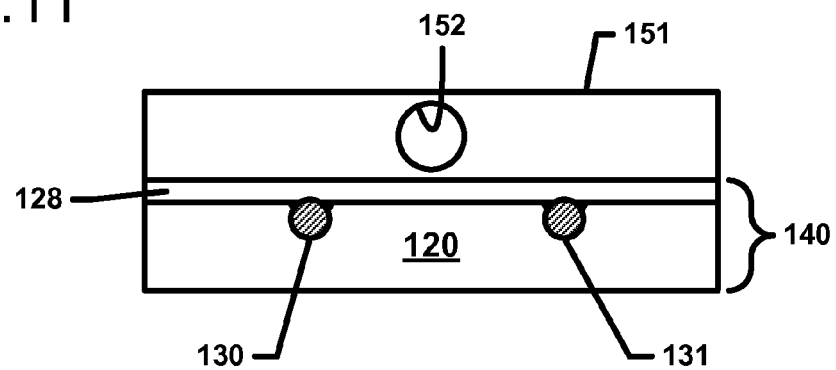
FIG. 11 is an end view of an example sensor module including the precursor sensor body of FIG. 10 and an example component body.
Figure 12:
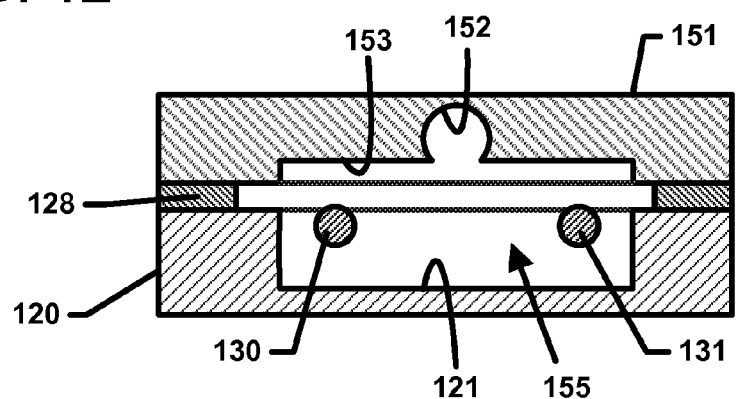
FIG. 12 is a cross-sectional view of the sensor module of FIG. 11 taken through the test chamber of the sensor module.

FIGS. 11 and 12 show the result of the join operation 111 of the manufacturing process 100 of FIG. 1. The join operation 111 attaches the precursor sensor body 140 to a component body 151 to form a sensor module 150. In some implementations, the component body 151 includes a molded carrier. In other implementations, the component body 151 includes a laminated member. Joining the precursor sensor body 140 and the component body 151 closes the test chamber 155.

The component body 151 defines a passage 152 extend at least from one end of the component body 151 to the test chamber aperture 129 in the rigid layer 128 of the precursor sensor body 140. The passage 152 provides an inlet at one end of the sensor module 150 that leads to the test chamber 155. In some implementations, the component body 150 includes a skin-piercing member that is configured to extend and retract through the passage 152 to take the blood sample.

Additional details regarding example sensor fibers suitable for use in sensor modules manufactured as described above can be found in U.S. Pat. Nos. 5,264,105; 5,356,786; 5,262,035; and 5,320,725, the disclosures of which are incorporated by reference herein. Further examples of sensor fibers are described in U.S. application Ser. No. 13/129, 325, filed May 13, 2011, and titled "Electrochemical Sensor Module," the disclosure of which is incorporated by reference herein. Other examples of sensor fibers are described in PCT Publication Nos. WO 2009/032760 and WO 2009/ 051901, the disclosures of which are incorporated by reference herein. Additional details regarding example sensor modules can be found in U.S. Provisional Application No. 61/430,384, filed Jan. 6, 2011, and titled "Sensor Module with Enhanced Capillary Flow," the disclosure of which is hereby incorporated herein by reference.

The above specification provides examples of how certain aspects may be put into practice. It will be appreciated that the aspects can be practiced in other ways than those specifically shown and described herein without departing from the spirit and scope of the present disclosure.

The invention claimed is:

1. A method of installing sensors in sensor modules, the method comprising:
   providing a first wafer and a continuous length of at least a first composite sensor fiber;
   removing material from the first wafer to form features of a plurality of precursor sensor bodies;
   disposing at least the first composite sensor fiber across the features of the precursor sensor bodies;
   coupling a rigid body to the first wafer;
   separating the coupled first wafer and rigid body into a plurality of precursor sensor bodies by cutting the first wafer, the rigid body, and the first composite sensor fiber into segments; and
   depositing conductive tracings on the first wafer prior to disposing the first composite sensor fiber across the features of the precursor sensor bodies.

2. The method of claim 1, further comprising:
   providing a continuous length of a second composite sensor fiber; and
   disposing the second composite sensor fiber across the features of the precursor sensor bodies adjacent to the first composite sensor fiber;
   wherein separating the coupled first wafer and rigid body into the plurality of precursor sensor bodies also includes cutting the second composite sensor fiber into segments.

3. The method of claim 2, wherein the segments of the first composite sensor fiber form working electrodes and the segments of the second composite sensor fiber form counter electrodes.

4. The method of claim 1, wherein removing material from the first wafer to form features of the plurality of precursor sensor bodies comprises etching the first wafer to form the features.

5. The method of claim 1, wherein removing material from the first wafer to form features of the plurality of precursor sensor bodies comprises removing the material to form a well for each precursor sensor body to be formed.

6. The method of claim 5, wherein coupling the rigid body to the first wafer comprises aligning apertures in the rigid body with the wells defined in the first wafer to form test chambers.

7. The method of claim 6, further comprising joining each of the precursor sensor bodies to a component body that closes each respective test chamber.

8. The method of claim 1, further comprising joining each of the precursor sensor bodies to a component body that includes a skin-piercing member.

9. The method of claim 1, wherein removing material from the first wafer to form the features of the precursor sensor bodies comprises forming multiple rows of the features of the precursor sensor bodies, each row including features of multiple precursor sensor bodies.

* * * * *